United States Patent [19]

Sasa

[11] Patent Number: 4,667,691

[45] Date of Patent: May 26, 1987

[54] DEVICE FOR CLEANING CHANNELS OF AN ENDOSCOPE

[75] Inventor: Hiroyuki Sasa, Hachioji, Japan

[73] Assignee: Olympus Optical Co., Ltd., Japan

[21] Appl. No.: 900,259

[22] Filed: Aug. 25, 1986

Related U.S. Application Data

[63] Continuation of Ser. No. 591,534, Mar. 20, 1984, abandoned.

[30] Foreign Application Priority Data

Apr. 5, 1983 [JP] Japan .................................. 58-59700
May 27, 1983 [JP] Japan .................................. 58-93855

[51] Int. Cl.$^4$ .................................................. B08B 3/08
[52] U.S. Cl. ............................ 134/169 C; 134/168 R; 222/309
[58] Field of Search ............... 422/33; 128/4, 6; 134/96, 99, 21, 22.12, 22.18

[56] References Cited

U.S. PATENT DOCUMENTS

| Re. 19,335 | 10/1934 | Uroukoff | 134/166 X |
| 543,477 | 7/1895 | Frye | 134/169 C X |
| 2,205,875 | 6/1940 | Coffey et al. | 222/309 |
| 2,709,025 | 5/1955 | Scott | 222/383 X |
| 2,849,159 | 8/1958 | Kaufmann | 222/383 X |
| 3,149,753 | 9/1964 | Forsyth | 222/309 X |
| 3,192,969 | 7/1965 | Baruch et al. | 222/309 X |
| 3,211,335 | 10/1965 | Shapiro | 222/309 X |
| 3,403,813 | 3/1969 | Gilmont | 222/309 X |
| 3,688,783 | 9/1972 | Owens | 134/169 R X |
| 3,730,398 | 5/1973 | Goda | 222/309 |
| 3,963,438 | 6/1976 | Banez | 21/58 |
| 4,294,271 | 10/1981 | Intrater et al. | 134/169 C X |
| 4,299,244 | 11/1981 | Hirai | 134/166 C X |

FOREIGN PATENT DOCUMENTS

| 538407 | 3/1957 | Canada . |
| 0071058 | 2/1983 | European Pat. Off. . |
| 7835596 | 5/1979 | Fed. Rep. of Germany . |

Primary Examiner—Harvey C. Hornsby
Assistant Examiner—Frankie L. Stinson
Attorney, Agent, or Firm—Ostrolenk, Faber, Gerb & Soffen

[57] ABSTRACT

A device for cleaning channels of an endoscope has its main body in which a first check valve for permitting merely suction of a liquid detergent into said main body, a syringe for effecting suction and discharge of the liquid detergent and a second check valve for permitting only discharge of the liquid detergent from said main body are provided so that the channels can be cleaned by feeding the liquid detergent thereinto through liquid feed tubes. Further including a transfer valve, a pluraltiy of channels can be selectively and switchably cleaned. In addition, a filter apparatus is provided in the device so as to be able to prevent foreign matters contained in the liquid detergent from entering the channels of the endoscope.

20 Claims, 9 Drawing Figures

DEVICE FOR CLEANING CHANNELS OF AN ENDOSCOPE

This application is a continuation of application Ser. No. 591,534 filed Mar. 20, 1984, now abandoned.

BACKGROUND OF THE INVENTION

The present invention relates to a device for cleaning channels of an endoscope which is used for cleaning various channel which are formed in an endoscope.

A variety of channels which are utilized for air and liquid feed to coeloma, suction of coeliac fluid and the like are commonly formed in an endoscope. Therefore, when cleaning an endoscope after used, it is necessary to clean the interior of the channels as well as the exterior thereof. The wording "cleaning" used herein means decontamination of the interior of channels which includes steps of washing with water, disinfection with a liquid disinfectant after the endoscope has been washed water and washing with water after the endoscope has been disinfected. These steps are normally effected in the order stated. In a conventional method for cleaning the channels, it is necessary to connect a tube for feeding a liquid detergent to a mouthpiece of each of the channels and then to place the connection in a communication condition by opening a fluid valve of each of the channels. These operations are required to be effected individually for each of the channels and are troublesome and timeconsuming. In addition, according to the conventional cleaning method, there is the possibility of obtaining imperfect cleaning of all parts of a valve body and portions covered by a valve body in a cylinder, which is a serious problem particularly in an endoscope.

To solve the problem, the applicant has proposed a device for cleaning channels of an endoscope as EPC Patent Application No. 82 106 100.9 (filed on 08.07.82) [Laid-Open Patent Publication No. 71058 (laid-open on 09.02.83)]. In the device of the application, a cleaning liquid is fed to channels of an endoscope from both an air-liquid feed cylinder and a suction cylinder to clean both the inner circumferential surfaces of the channels and the cylinders concurrently therewith. Specifically, removing fluid valves which are interposed within the air-liquid feed and the suction cylinders, adapters are mounted on the evacuated opening thereof. Then, a liquid feed tube which is connected to the adapter is connected to a liquid feed pump. Liquid is fed from the pump through the adapter to each of the channels. Thus, the cleaning operation is effected by feeding the liquid from the cylinders to a liquid feed channel, an air feed channel and a suction channel of an endoscope and discharging the liquid from a suction port and a nozzle of a distal end of the endoscope and an air feed port, a liquid feed port and a suction port of a connector assembly.

However, channel conduits of the endoscope vary in an inner diameter. Specifically, the endoscope is constructed in such a manner that although generally, an air and a liquid feed channel conduits are small and a suction channel conduit is large in size, these channel conduits arranged in an insertion body of the endoscope are still smaller than a channel conduit in a light guide cable in size. Accordingly, even when liquid is fed from the aforesaid cylinders which permit these channel conduits to communicate with one another, the liquid flows into a conduit which has a smaller flow resistance in a concentrated manner but does not flow sufficiently into a conduit which has a high flow resistance. After all, it is impossible to assure a reliable and thorough cleaning of all channel conduits of the endoscope.

SUMMARY OF THE INVENTION

In view of the foregoing, it is an object of the invention to provide a device for cleaning channels of an endoscope which is easily interconnected to each of the channel conduits and permits a reliable and thorough cleaning of the interior of each of the channel conduits and cylinders for fluid valves.

According to the invention, a plurality of connecting port bodies are provided on the cleaning device main body through a transfer valve, a liquid feed tube which is connected to each of various port bodies of the endoscope is provided on each of the plurality of connecting port bodies and a syringe is connected to the cleaning device main body. Detergent liquid in a liquid tank is drawn into the syringe by operating the latter and is fed into each of the channels of an endoscope through the liquid feed tube. Accordingly, it is possible to easily and reliably clean the interiors of the channel conduits and the cylinders for the fluid inlet valves of the endoscope. In addition, since the detergent liquid is supplied under pressure through a transfer valve, it can be conducted into all the channels over their entire length even when the channel conduits differ in their inner diameters, with a simple construction of the cleaning device, resulting in a reduced cost.

In addition, according to the invention, a filter apparatus for removing foreign matters contained in a liquid detergent is provided in a passage between the suction port of a liquid feed apparatus which picks up the liquid detergent in a liquid detergent tank and the channel conduits of the endoscope to prevent foreign matters from entering various channels of the endoscope which are generally of a small diameter. As a result, there is no possibility that after the channels are cleaned, foreign matters remain so that an air feed, liquid feed and suction operation may not be conducted reliably.

DESCRIPTION OF A PREFERRED EMBODIMENT

Figure 1:
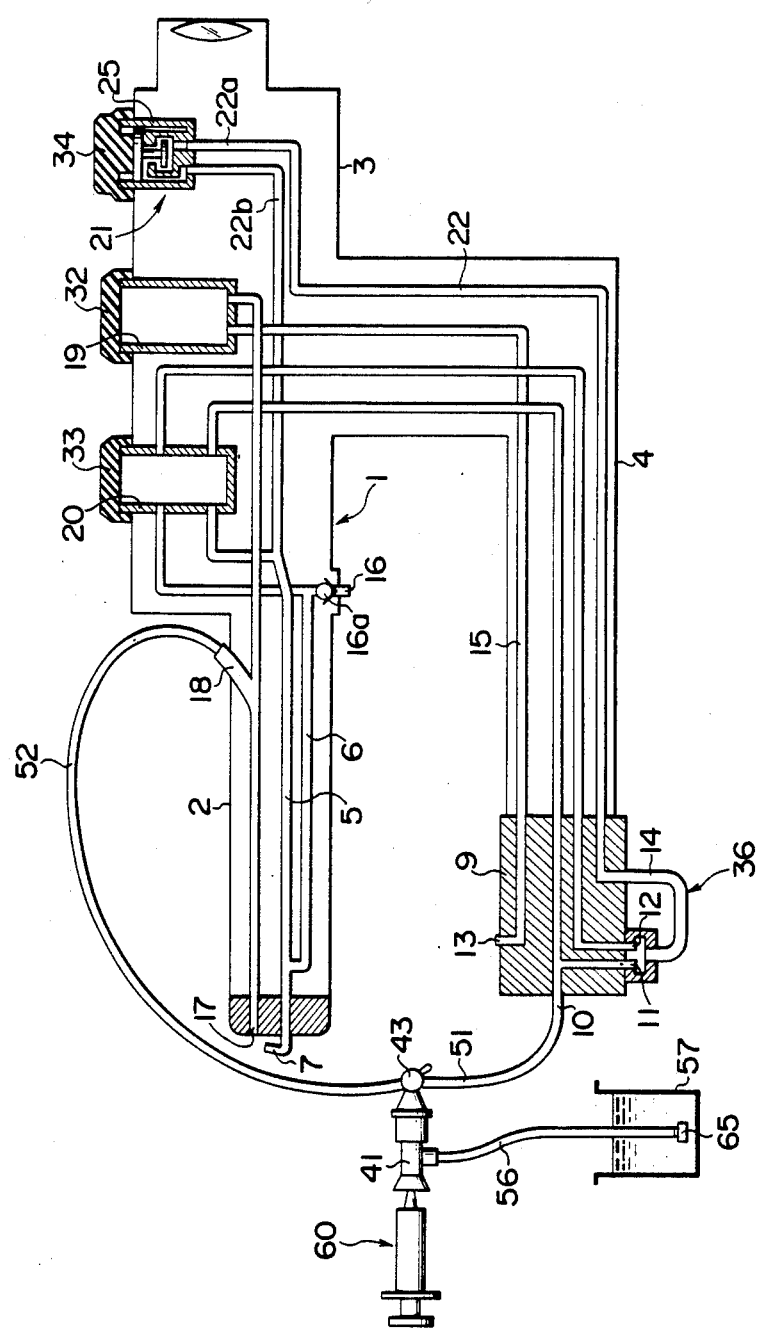
FIG. 1 is a diagrammatic arrangement view of a device for cleaning channels of an endoscope which is in use, illustrating one embodiment of the invention.

Referring to FIG. 1, an endoscope 1 comprises an insertion body 2, an operation body 3 and a light guide cable 4. A variety of channels are built into the endoscope as follows. An air and a liquid feed channels 5, 6 extend through the insertion body 2, operation body 3 and light guide cable 4. The downstream ends of the air and the liquid feed channels 5, 6 join in a nozzle 7 for supplying air and liquid which is provided on the terminal end of the insertion body 2. The nozzle 7 is provided in such a manner that its tip is directed to the outer surface of an observation window (not shown) to spray detergent liquid and air thereto. A connector 9 is provided on an extended end of the light guide cable 4. On the connector 9 are provided a first and a second air feed port bodies 10, 11 which communicate with the air feed channel 5, a liquid feed port body 12 which communicates with the liquid feed channel 6, a suction port body 13 which communicates with a suction channel which will be described later and a gas feed port body 14. The first air feed port body 10, when the connector 9 is mounted on a light source apparatus (not shown) for an endoscope, is to be connected to an air supply pump provided in the light source apparatus. The second air feed port body 11 and the liquid feed port body 12 are to be connected to a feed liquid tank (not shown). Additionally, the suction port body 13 is to be connected to a suction apparatus (not shown).

A suction channel conduit 15 extends through the insertion body 2, the operation body 3 and the light guide cable 4. The suction channel conduit 15 is arranged to provide a channel for guiding a treating implement at its distal end. The distal end of the conduit 15 is open at a suction port 17 on the distal end plane of the insertion body 2. The proximal end of the treating implement guiding channel opens outwardly in the operation body 3 to form a forceps port body 18 on which a forceps plug (not shown) is detachably mounted. An auxiliary liquid feed port body 16 includes a check valve 16a.

Additionally, the treating implement guiding channel is connected through a cylinder 19 of a suction valve to the proximal end of the suction channel 15. A cylinder 20 of an air-liquid feed valve is disposed between the air feed channel 5 and the liquid feed channel 6. The valve cylinders 19, 20 are arranged closely juxtaposed to the flank of the operation body 3. A gas feed valve 21 is arranged in the proximity of the valve cylinders 19, 20. A channel conduit 22 is connected to the valve 21 and is also connected to the air feed channel conduit 5 which is between the cylinder 20 and the nozzle 7 and a gas feed port body 14.

Figure 2:
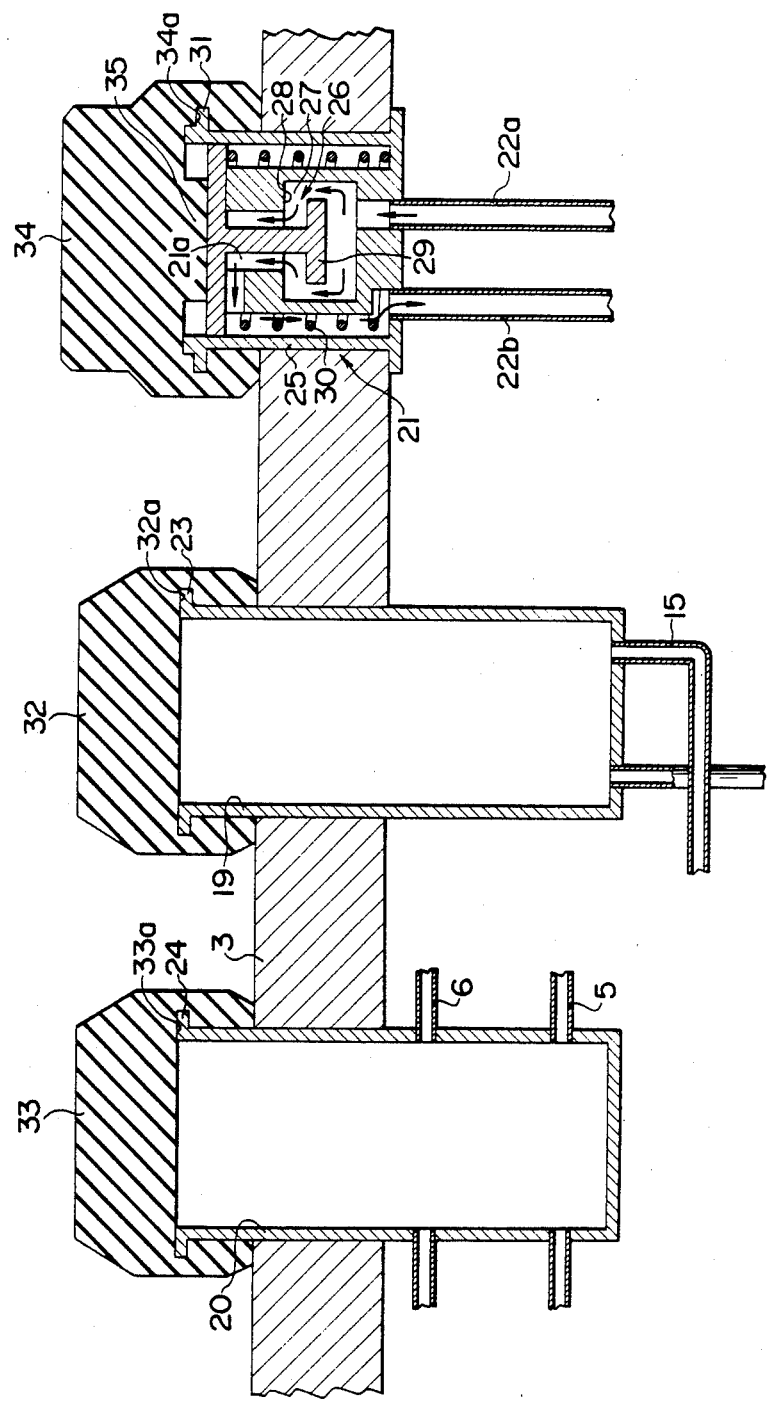
FIG. 2 is a partially enlarged sectional view of an operation end of the endoscope shown in FIG. 1.

Details of the cylinders 19, 20 and the valve 21 are illustrated in FIG. 2. The suction valve cylinder 19 has a bottomed cylindrical shape and a flange 23 is integrally formed on the opening edge of the cylinder 19. The air-liquid feed valve cylinder 20 has a bottomed cylindrical shape and a flange 24 is formed on the opening edge of the cylinder 20. The gas feed valve 21 comprises a cylinder 25 and a valve mechanism 26 which is mounted in the cylinder 25. A valve chamber 27 is formed within the cylinder 25 concentrically therewith. A valve body 29 is mounted in the chamber 27 so as to be movable toward or away from a valve seat 28. The valve body 29 is normally urged by a coiled spring 30 in the direction of approaching to the valve seat 28 or closing the valve to shut off a passage 21a which connects the upstream side path 22a to the downstream side path 22b of the gas feed channel 22. A flange 31 is integrally formed on the opening edge of the cylinder 25. Plugs 32, 33 are mounted on respective cylinders 19, 20 to close their opening ends. On the circumferential surfaces of plugs 32, 33 are formed grooves 32a, 33a which respectively engage the flanges 23, 24 so that plugs 32, 33 do not come off even when an internal pressure of the cylinders 23, 24 rises. A plug 34 is mounted on the cylinder 25 of the valve 21 to close the opening end thereof. A projection 35, which is centrally provided within the plug 34, acts, when the plug 34 is mounted on the cylinder 25, to permit the passage 21a to be opened by pushing the valve body 29 inwardly against the restoring force of the coiled spring 30 to move away the valve body 29 from the valve seat 28. The plug 34 is further provided with a groove 34a which engages the flange 31 for the same purpose as the aforesaid.

Figure 3:
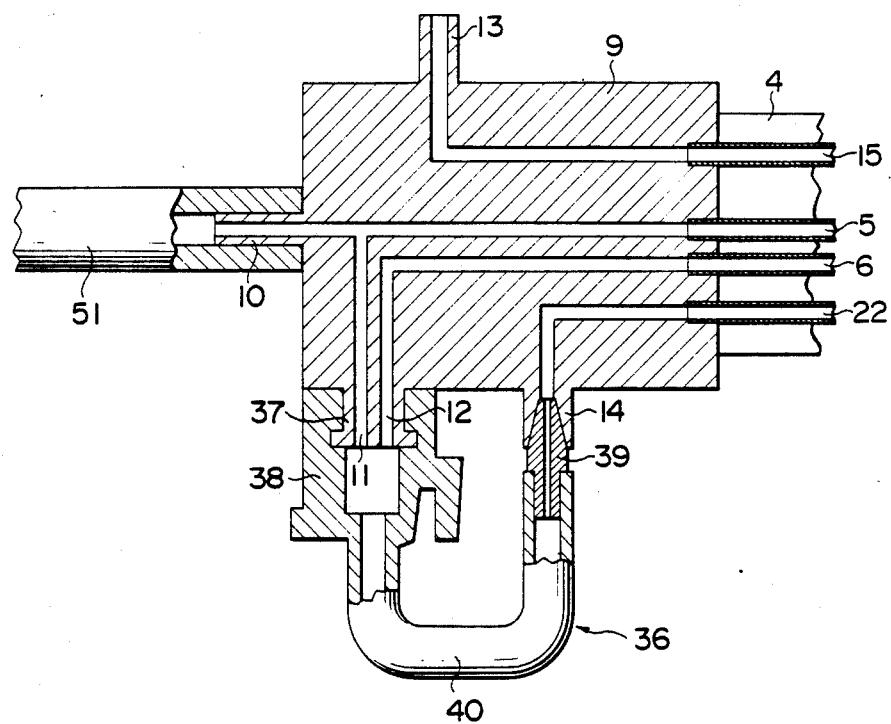
FIG. 3 is a partially cutaway enlarged sectional view of a communicating member for channels shown in FIG. 1.

In FIG. 3, the second air feed port body 11, the liquid feed port body 12 and the gas feed port body 14 communicate with one another by means of a channel communicating member 36. The communicating member 36 comprises a connecting port body 38 which is fitted to an inlet mouthpiece 37 including the second air feed port body 11 and the liquid feed port body 12, an insertion port body 39 which is fitted to the gas feed port body 14 and a communicating tube 40 which connects the port body 38 to the port body 39.

A cleaning device of an embodiment of the invention for cleaning channels of an endoscope which is constructed as described above will be described with reference to FIGS. 1 and 4. A main body 41 of the cleaning device is substantially cylindrical in shape and is formed of a synthetic resin or glass in a liquid tight construction. The main body 41 includes a tapered body in which a check valve 42 for allowing only discharge of a liquid detergent from the body 41 is interposed at the pointed end of the tapered body and a transfer valve 43 which is disposed beyond the check valve 42 through the tapered pointed end of the body. The transfer valve 43 comprises a cylindrically shaped valve case 44, a valve body 45 which is rotatably disposed within the valve case 44 and a lever 46 for rotating the valve body 45. A liquid supply port 47 is provided in the valve case 44 which communicates with the main body 41. A first and a second connecting inlet bodies 48, 49 are provided on the case body 44 in the positions at 90 degrees to the axis of the port 47. The valve body 45 has a communicating portion 50 which is obliquely cut off so as to selectively permit the port 47 to be communicated with the first and the second connecting inlet bodies 48, 49 by rotating the valve body 45. The first and the second connecting inlet bodies 48, 49 are connected to the base ends of a first and a second liquid feed tubes 51, 52, respectively. In addition, the main body 41 is provided with a fitting port 53 at the base end thereof which is connected to a syringe to be described later. An inlet port body 54, which is provided in the intermediate part of the main body 41, is connected through a connecting ring 55 to a liquid inlet tube 56. The tube 56 communicates with a liquid tank 57 which contains a liquid detergent. A check valve 58 which permits only suction of a liquid detergent into the main body 41 is provided in the inlet port body 54. A body 59 of the syringe 60 has a connecting port body 61 at the front end thereof which is detachably connected to the fitting port 53 of the main body 41. A piston 62 is movably inserted into the body 59.

Figure 5:
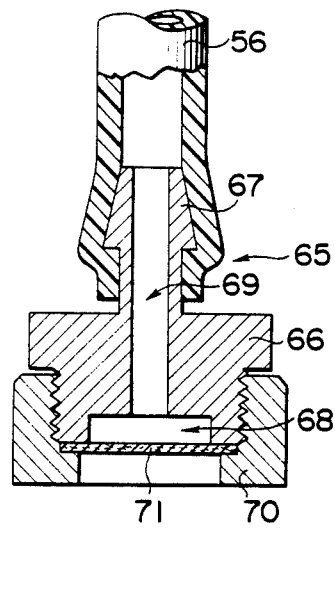
FIG. 5 is an enlarged sectional view of a filter apparatus shown in FIG. 1.

A filter apparatus 66 having a filter body 65 as shown in FIG. 5, is connected to the distal end opening or the suction port of the tube 56. A mouthpiece 67 is provided on one end plane of the filter body 66 and a recess 68 is formed on the other end plane thereof. A suction passage 69 is provided between the filter body 66 and the mouthpiece 67. In addition, a ring shaped cap 70 is threadedly mounted on the other end plane of the filter body 66. A filter is held between the cap 70 and the filter body 66 so as to cover the recess 68. The filter 71 is a 40 or more per inch mesh screen, for example.

In operation, as shown in FIG. 1, the plugs 32, 33, 34 are mounted on the cylinders 19, 20, 25 of the operation end 3 (also see FIG. 2). The connecting port body 38 of the channel communicating member 36 is fitted into the inlet mouthpiece 37 of the connector 9 and the insertion port body 39 is fitted into the gas feed port body 14 (FIG. 3). In addition, the first liquid feed tube 51 is connected to the first air feed port body 10 of the connector 9 and the second liquid feed tube 52 is connected to the forceps port body 18 of the operation body 3.

Under the above mentioned condition, when the piston 62 is driven backwardly (withdrawn from syringe body 59), a negative pressure is created within the main body 41 to close the first check valve 42 and to open the second check valve 58. Accordingly, the liquid detergent in the tank 57 is picked up through the filter 71 into the tube 56 and is admitted from the tube 56 through the suction port 54 into the main body 41 and the syringe body 59. In addition, since the liquid detergent is admitted through the filter 71 into the syringe body 59, even if foreign matters are mixed in the tank 57, they would be removed by the filter 71 so that they will not be drawn in the syringe body 59. When the piston 62 is driven forwardly (into syringe body 59), a positve pressure is created within the main body 41 to open the first check valve 42 and to close the second check valve 58. Accordingly, the liquid detergent within the main body 41 and the syringe body 59 is delivered under pressure from the port 47. At this time, while the transfer valve 43 is under the condition that the port 47 communicates through the communicating portion 50 with the first connecting port body 48, as shown in solid lines in FIG. 4, the liquid detergent is fed from the port body 48 through the first liquid feed tube 51 to the first air feed port body 10 of the connector 9. The liquid detergent which is fed to the first air port body 10 flows through the air feed channel 5 and is introduced into the valve cylinder 20. A part of the liquid detergent flows through the second air feed port body 11. Accordingly, the liquid detergent is distributed by the communicating member 36 to the liquid feed port body 12 and the gas feed port body 14 and is introduced into the cylinders 20, 21 through the liquid feed channel 6 and the gas feed channel 22. The liquid detergent introduced into the cylinder 20 issues from the nozzle 7 through the air feed channel 5 and the liquid feed channel 6 in the insertion body 2. The liquid detergent introduced into the cylinder 21 flows from upstream channel path 22a to the valve chamber 27 and detours within the valve mechanism 26 in its open condition to the downstream channel path 22b (FIG. 2). Thereafter, the liquid detergent joins in the middle of the channel 5 to further issue from the nozzle 7. As a result, the interiors of the channels 5, 6, 22 over their entire length are cleaned. At the same time, the interior of the cylinder 20 and the valve 21 can be cleaned.

Figure 4:
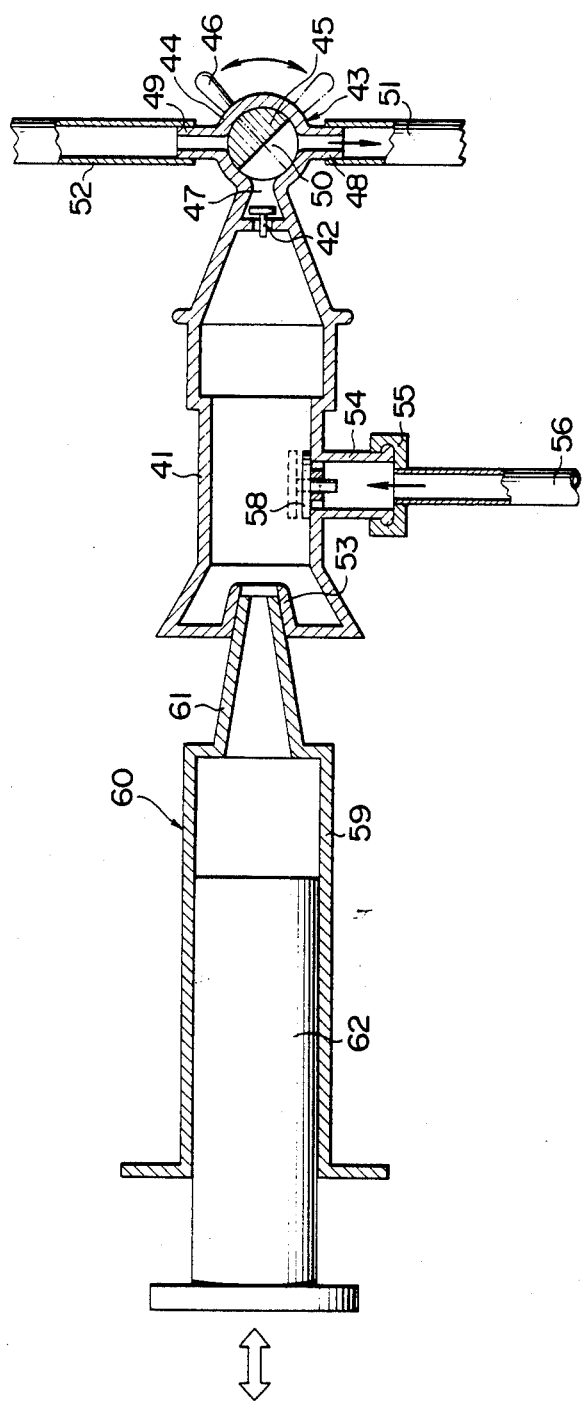
FIG. 4 is an enlarged sectional view of the cleaning device shown in FIG. 1.

Subsequently, when the valve body 45 is rotated as shown with a broken line in FIG. 4 by operating the lever 46, the port 47 communicates through the communicating portion 50 with the second port body 49. Under this condition, a liquid detergent is drawn in the tank 57 through the filter apparatus 65 by operating the piston 62 in a manner similar to the aforesaid. Thereafter, the liquid detergent is supplied under pressure from the second port body 49 through the second tube 52 to the forceps port body 18. At this time, the liquid detergent is distributed into the insertion body 2 and the operation body 3. The liquid detergent fed into the insertion body 2 issues from the suction port 17 through the suction channel 15. The liquid detergent flowing through the operation end 3 is introduced into the cylinder 19 and then flows through the suction channel 15 in the light guide cable 4 to issue from the suction port body 13 of the connector 9. Accordingly, the interior over the entire length of the suction channel 15 is cleaned and simultaneously the interior of the cylinder 19 is also cleaned. After all, all channels of the endoscope are cleaned.

While in the cleaning operation, even if foreign matters are included in the liquid detergent within the tank 57 they will be reliably removed by the filter 71 so that they will not remain within various channels 5, 6, 15, 22 by being fed.

In the above embodiment, the first liquid feed tube 51 is connected to the first air feed port body 10 and the second liquid feed tube 52 is connected to the forceps port body 18, in order to supply a liquid detergent. However, this is merely one example of how the invention can be used. By way of another example, a liquid detergent may be fed from either the suction port body 13 or the suction port 17 to clean the suction channel 15. Then, it may be consecutively fed from the second air feed port body 11, the liquid feed port body 12 and the gas feed port body 14. Additionally, it may be possible to feed a liquid detergent from the cylinders 19, 20, 25 in the operation end 3.

In addition, the above-mentioned cleaning device is for use in an endoscope provided with the gas feed valve 21. However, it may be also applied to an endoscope which does not have the valve 21.

The cleaning liquid used in the above embodiment may be water or detergent. When detergent is used, the cleaning operation is generally referred to as sterilization. However, the word "cleaning" as used herein includes both water cleaning and sterilization.

Figure 6:
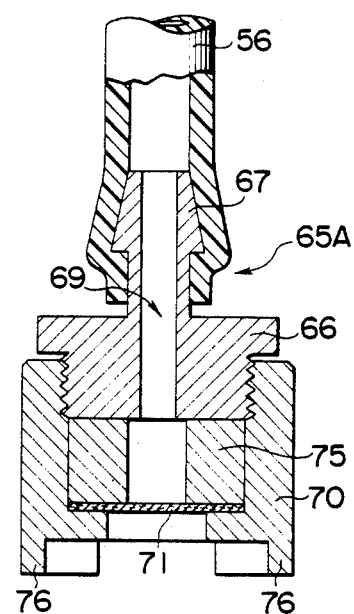
FIGS. 6 and 7 are enlarged sectional views illustrating examples other than the filter apparatus shown in FIG. 5.
Figure 7:
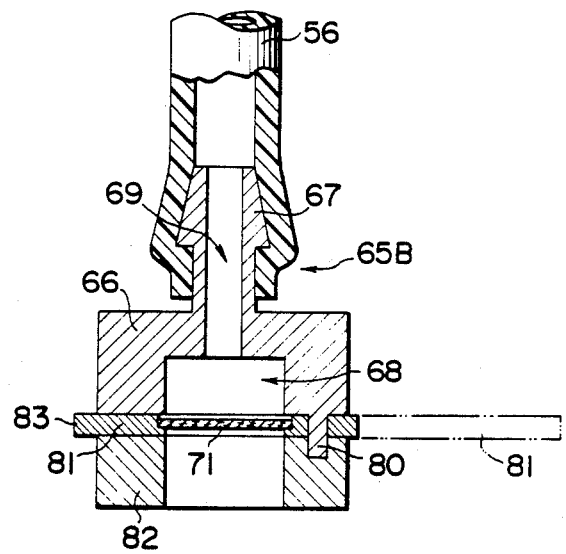

In addition, the filter apparatus 65 may be constructed as shown in FIGS. 6 and 7. Specifically, the filter apparatus 65A shown in FIG. 6 holds a filter 71 between a filter body 66 and a cap 70 with a dead weight 75 of a cylindrical form and a plurality of legs 76 are projectedly provided on the end surface of the cap 70. With the construction just described, the filter apparatus 65 is reliably submerged to the bottom of the tank 57 by weight of the dead-weight 75 and the cap 70 abuts against the bottom of the tank 57 through the legs 76 so that the suction passage 69 will not be blocked.

In a filter apparatus 65B shown in FIG. 7, a rod 80 is projected from the end plane of a filter body 66 and a mounting plate 81 on which a filter 71 is held is rotatably mounted on the rod 80. A filter cap 82 of a cylindrical form of substantially the same outer size as that of the filter body 66 which cap holds the mounting plate 81 together with the end plane of the filter body 66 is further mounted on the rod 80. A lever 83 which is projected from the outer periphery of the filter body 66 is provided on the mounting plate 81. With the construction described above, the mounting plate 81 is turned with the lever 83 as shown with chain lines in FIG. 7, whereby the filter 71 held on the mounting plate 81 can be readily cleaned or exchanged.

Further, the filter 71 may be provided in a place other than in the distal end or the suction port of the tube 56. What is essential is that anywhere may be good if the filter 71 is disposed between the suction port and the channels of the endoscope 1.

What is claimed is:

1. A device for cleaning channels of an endoscope, comprising:

a liquid tight main body for confining a cleaning liquid therein;

a first check valve provided in said main body for permitting suction of said cleaning liquid into said main body through a liquid inlet tube which communicates with a cleaning liquid tank when a negative pressure is created in said main body;

a second check valve provided in said main body for permitting discharge of said cleaning liquid from said main body when a positive pressure is created in said main body;

suction means secured to said main body for creating, at the option of the operator of said suction means, a negative or positive pressure in said main body so as to effect suction and discharge, respectively, of the cleaning liquid confined within said main body;

a plurality of connecting port bodies provided on said main body;

a transfer valve having a plurality of positions, said transfer valve operable in each of said plurality of positions to cause a respective one of said connecting port bodies to communicate with said second check valve; and a plurality of liquid feed tubes each having one end connected to a respective one of said connecting port bodies, the other ends of said liquid feed tubes respectively being for connecting to a plurality of channels of said endoscope including both an air or water feed channel and a suction channel, each of said respective plurality of channels having a different respective fluid flow characteristic, said transfer valve being operable to permit said cleaning fluid to flow through one said respective plurality of channels at a time, whereby a predetermined quantity of fluid may be directed through each respective plurality of channels.

2. A device according to claim 1, in which said transfer valve comprises a valve case in a hollow cylindrical shape which communicates with the interior of said main body and on which said plurality of connecting port bodies are provided; a cylindrical valve body housed within said valve case in an externally rotatable manner by means of a lever; and a communicating portion which is formed by a cut off part of said valve.

3. A device according to claim 1, in which said liquid inlet tube is detachably mounted by means of a suction port body which is provided on said main body and a connecting ring which is provided on one end of said tube.

4. A device according to claim 1, further including a filter apparatus provided in a passage between a suction port of said liquid feed tube and the channels of the endoscope for removing foreign matter contained in said cleaning liquid.

5. A device according to claim 4, in which said filter apparatus is mounted on the suction port of said liquid feed tube.

6. A device according to claim 4, in which said filter apparatus comprises a filter body on which a mouthpiece is projectedly provided which is fitted into the suction port of said fluid feed tube, a cap which is threadedly mounted on said filter body and a filter which is held between said filter body and said cap so as to cover the suction passage therebetween.

7. A device according to claim 6, in which a deadweight is held between the filter body and the cap together with said filter.

8. A device according to claim 6, in which a leg or legs are projectedly provided on the underside of said cap so that said cap abuts against said tank to prevent said suction passage from being blocked.

9. A device according to claim 4, in which said filter apparatus comprises a filter body on which a mouthpiece is provided which is fitted into the suction port of the liquid feed tube, a filter mounting plate which is rotatably fitted into the filter body at its one end and a filter which is removably fitted into said filter mounting plate so as to cover the suction passage.

10. A device according to claim 1, wherein said second check valve is formed in a first end of said main body and said suction means is a secured to a second end of said main body, opposite said first end.

11. A device for cleaning channels of an endoscope of the type having an insertion body with a port at a first end which is configured to be inserted into a cavity, the cleaning device comprising:

a liquid tight main body for confining a cleaning liquid therein:

a first check valve provided in said main body for permitting suction of said cleaning liquid into said main body through a liquid inlet tube which communicates with a cleaning liquid tank when a negative pressure is created in said main body;

a second check valve provided in said main body for permitting discharge of said cleaning liquid from said main body when a positive pressure is created in said main body;

suction means secured to said main body for creating, at the option of the operator of said suction means, a negative or positive pressure in said main body so as to effect suction and discharge, respectively, of the cleaning liquid confined within said main body;

a plurality of connecting port bodies provided on said main body;

a transfer valve having a plurality of positions, said transfer valve operable in each of said plurality of positions to cause a respective one of said connecting port bodies to communicate with said second check valve; and a plurality of liquid feed tubes each having one end connected to a respective one of said connecting port bodies, the other ends of said liquid feed tubes respectively being for connecting to a plurality of channels of said endoscope including both an air or water feed channel and a suction channel, which channels are remote from said first end of said insertion body, each of said respective plurality of channels having a respective fluid flow characteristic, said transfer valve being operable to permit said cleaning liquid to flow through only one of said respective plurality of channels at a time, whereby each of said respective plurality of channels are individually cleaned at a desired pressure and any contaminant lodged in any port opening at said first end of said insertion body is forced out said port opening to prevent contamination inwardly of said port opening.

12. A device according to claim 11, in which said transfer valve comprises a valve case in a hollow cylindrical shape which communicates with the interior of said main body and on which said plurality of connecting port bodies are provided; a cylindrical valve body housed within said valve case in an externally rotatable manner by means of a lever; and a communicating portion which is formed by a cut off part of said valve.

13. A device according to claim 11, in which said liquid inlet tube is detachably mounted by means of a suction port body which is provided on said main body and a connecting ring which is provided on one end of said tube.

14. A device according to claim 11, further including a filter apparatus provided in a passage between a suction port of said liquid feed tube and the channels of the endoscope for removing foreign matter contained in said cleaning liquid.

15. A device according to claim 14, in which said filter apparatus is mounted on the suction port of said liquid feed tube.

16. A device according to claim 14, in which said filter apparatus comprises a filter body on which a mouthpiece is projectedly provided which is fitted into the suction port of said fluid feed tube, a cap which is threadedly mounted on said filter body and a filter which is held between said filter body and said cap so as to cover the suction passage therebetween.

17. A device according to claim 16, in which a deadweight is held between the filter body and the cap together with said filter.

18. A device according to claim 17, in which a leg or legs are projectedly provided on the underside of said cap so that said cap abuts against said tank to prevent said suction passage from being blocked.

19. A device according to claim 14, in which said filter apparatus comprises a filter body on which a mouthpiece is provided which is fitted into the suction port of the liquid feed tube, a filter mounting plate which is rotatably fitted into the filter body at its one end and a filter which is removably fitted into said filter mounting plate so as to cover the suction passage.

20. A device according to claim 11, wherein said second check valve is formed in a first end of said main body and said suction means is a syringe secured to a second end of said main body, opposite said first end.

* * * * *